US00PP09099P

United States Patent [19]

Escande

[11] Patent Number: Plant 9,099

[45] Date of Patent: Apr. 4, 1995

[54] NECTARINE TREE—CRYSTAL RED

[76] Inventor: Jean L. Escande, 47500 Fumel, Saint Vite, France

[21] Appl. No.: 141,347

[22] Filed: Oct. 22, 1993

[51] Int. Cl.[6] ..... A01H 5/00
[52] U.S. Cl. ..... Plt./40.1
[58] Field of Search ..... Plt. 40.1

*Primary Examiner*—James R. Feyrer
*Attorney, Agent, or Firm*—Godfrey & Kahn

[57] ABSTRACT

A new and distinct variety of nectarine tree which is somewhat similar in its harvesting date with that of the Arctic Glo nectarine tree [U.S. Plant Pat. No. 7,884] which matures at approximately the same time of the season, but which is distinguished therefrom, and characterized principally as to novelty by producing fruit which have a larger size, firm flesh texture and an attractive skin color at commercial maturity.

1 Drawing Sheet

BACKGROUND OF THE NEW VARIETY

The present invention relates to a new and distinct variety of nectarine tree denominated varietally as Crystal Red and more particularly, to such a nectarine tree which bears a semi-freestone fruit which has a firm substantially white-colored flesh and attractive exterior coloration and which further is ripe for commercial harvesting and shipment approximately June 10 through 17 under the ecological conditions prevailing in the San Joaquin Valley of central California.

It has long been recognized that an important factor contributing to the success of any variety of nectarine tree bearing fruit for the fresh market is the propensity for the fruit to be attractive in appearance. Another important factor is that the variety bear fruit at a time when other fruit with the same desirable qualities is not normally available.

The present variety of nectarine tree, as noted above, is a semi-freestone fruit which has an attractive red skin color and which further is somewhat similar in its date of harvesting with that of the nectarine tree denominated varietally as "Arctic Glo" (U.S. Plant Pat. No. 7,884) but which is distinguishable therefrom and characterized principally as to novelty by producing fruit which have a larger size, exceptional flesh firmness at commercial maturity, and a noteworthy, sweet flavor.

ORIGIN AND ASEXUAL REPRODUCTION OF THE NEW VARIETY

This new and distinct variety of nectarine tree is a hybrid nectarine tree resulting from the cross-pollination of one of the stock nectarine trees of the inventor which is identified by the alpha-numeric designator 481, and which is of unknown parentage, with that of the "Snow Queen" nectarine tree [believed unpatented]. The parent tree 481 is a proprietary tree which has not been released to the public. Cross-pollination of the present variety took place at the inventor's farm which is located near Saint Vite, France. The selection from this cross-pollination was germinated and sections of budwood were removed from the original offspring and grafted into commercial root stock which was then growing within the cultivated area of the same farm. The fruit, and grafted trees have been compared and contrasted over the last several years with that of the original cross-pollinated offspring and it has been determined that this asexual propagation resulted in a nectarine tree being produced which possesses the same distinctive characteristics as the originally selected offspring resulting from the stated crosos-pollination.

As compared with the seed parents, the present variety of nectarine tree produces fruit which are larger in size and more highly colored than those of the parents.

SUMMARY OF THE NEW VARIETY

The new variety of nectarine tree described herein is characterized principally as to novelty by producing semi-free stone fruit which are mature for commercial harvesting and shipment approximately mid-June under the ecological conditions prevailing in the San Joaquin Valley of central California. This date of harvesting is approximately at the same time as the Arctic Glo nectarine tree (U.S. Plant Pat. No. 7,884), but the new variety is distinguishable from the Arctic Glo nectarine tree by producing fruit which are generally considered to be more highly colored and larger in size then the Arctic Glo nectarine tree and which further has a noteworthy sweet flavor.

BRIEF DESCRIPTION OF THE DRAWING

The accompanying drawing is a color photograph of five mature fruit of the subject variety; one of which has been divided in the suture plane to show the flesh and stone characteristics, together with a twig bearing typical leaves showing the characteristic colors thereof, all of the subject variety.

DETAILED DESCRIPTION

Referring more specifically to the polmological details of this new and distinct variety of nectarine tree, the following has been observed under the ecological conditions prevailing at the applicant's licensee's orchard which is located near Visalia, Calif. All major color code designations are by reference to the dictionary of color by Maerz & Paul, First Edition, or alternatively, by reference to the Inter-Society Color Council, National Bureau of Standards Color Charts. Common color names are also employed occasionally.

TREES

Size:

*Generally.*—Medium to large depending upon pruning practices. The present trees, which are four years old, were nursery propagated on Nemaguard peach root stock. These trees now have a crown which has a size of approximately 96 to 115 inches in width; and are approximately 10 foot to 10.5 feet in height. These same trees were pruned to a height of approximately 7 to 8 feet during the winter of the 1993 through 1994 and now have developed new growth which has a length of approximately 3 to 3.5 feet.

Vigor: Vigorous, and hardy when grown under typical San Joaquin Valley ecological conditions.

Figure: Upright and spreading, the eventual form of the tree will be determined by pruning practices. The present trees are trained to an open-vase system. Most of the trees have now developed four scaffolds.

Productivity: Productive, and normally fruitful at all bearing points.

Regularity of bearing: Regular.

TRUNK

Size:

*Generally.*—Large, and considered sturdy. Four year old trees measured at the licensee's orchard range in size from 9.5 to 10 centimeters in diameter.

Surface texture: Coarse and checked with large amounts of scarfskin being present.

Color:

*Generally.*—Dark, grey-brown [7-C-9]. This color is not particularly distinctive of the subject variety and is indistinguishable from the seed parents.

Lenticels:

*Generally.*—Numerous, relatively large, oval, lenticels are present and which range in size from 4 to 8 millimeters in width, [horizontally] and from 1 to 2 millimeters in height [vertically].

BRANCHES

Size:

*Generally.*—Large and sturdy. These appears indistinguishable from the seed parents.

Surface texture: Checked and bark coarse.

Internode length: Considered average, and having a range of length of about 16 to 29 millimeters when compared with average sized, current season hanger wood.

Bark color:

*Generally.*—Dark, grey-brown [15-A-10]. The color is not particularly distinctive of the new variety. Some lighter colored wood may be found [15-C-9]. The color of the current seasons shoots is pale green [19-J-6]. Further, the shoot surfaces which are exposed to direct sunlight are often tinged rose to purple in color [5-I-3] to [5-J-4]. Additionally, expanding shoot tips take on a light greenish-yellow color [18-L-4].

Flowering branches:

*Thickness.*—Average.

Density of buds: Dense.

LEAVES

Size:

*Generally.*—Large.

*Average length.*—Approximately 15.2 through 18.6 centimeters, including the petiole.

*Average width.*—Approximately 4.1 through 5.2 centimeters.

Leaf:

*Thickness.*—Considered normal.

*Form.*—Generally — Lanceolate.

Surface texture:

*Upper surface.*—Glabrous.

*Marginal form.*—Crenate having low uniform crenatons of average size and further having double crenations often occurring at mid-margin. Additionally, the leaf margins are considered only slightly undulate.

*Leaf glands.*—Shape — Reniform.

*Numbers.*—Generally two to four glands are present on petiole or at the base of the leaf margin. The base glands occasionally appear stalked.

*Color.*—Light, green-yellow when young, [17-L-6], and which darkens with senescence.

*Size.*—Large.

*Location.*—Alternate. On occasion, one or two additional glands can be found on the lower leaf margin.

*Stipules.*—Generally — Few in number, and having a variable length of approximately 7 through 9.5 millimeters. The stipules are considered to be linearly lanceolate in form. The color of the stipules is pale-green [19-I-7]. Marginal form — Coarsely serrate.

*Leaf vein.*—Color — Light green, [21-J-6] [120. m. YG].

*Leaf color.*—Bottom surface — a pale, dull green [22-K-4], [125. m. 01 G].

*Top surface.*—Dark green [23-L-K], [126 d. O1G].

*Mid-vein — color.*—A pale yellow-green, [17-G-5].

Leaf blade profile: Generally folded upwardly especially at mid-vein.

*Leaf blade.*—Tip — The leaf blade tip is generally recurved downwards and is considered acuminate. Angle — The angle of the leaf blade at the base, is normally at a right angle. Ratio of length to width — Considered high.

*Petiole.*—Generally — Considered average in size; approximately 9 to 12 millimeters in length and, 1.5 to 2 millimeters in the thickness.

*Color.*—Light green [17-J-7] and having a slightly darker color within the petiole groove.

*Shape.*—Grooved.

Date of leaf bud burst:

*Generally.*—Average as compared to similar varieties.

FLOWERS

Blooming time: Early to mid-season as compared to other common nectarine tree varieties.

Date of full bloom: February 26 through March 5 at Visalia, Calif.

Flower size:

*Generally.*—Average as compared to flowers of other nectarine varities blooming in the same season.

Dormancy: The present variety normally requires a dormancy period of approximately 500 hours at temperatures below 45° F.

Flower buds:

*Generally.*—Hardy, and well developed.

Flowers:

*Generally.*—Showy type.

*Color.*—The petal margins are a light pink, [1-C, Plate 50]. The petal base is a darker pink, [G-12, Plate 51].

Flower fertility: Considered self-fruitful.

Duration of flowering: Average as compared to other nectarine varieties.

Petals:

*Shape.*—Rounded, and uniform.

*Numbers.—Generally* 5.

Pistils:

*Numbers.*—Always 1.

Stigma:

*Generally.*—The stigma is normally at the same level as the anther.

Stamens:

*Generally.*—The length of the stamens are normally equal to the length of the petals.

Anthers:

*Generally.*—Pollen is normally present on each of the anthers.

Ovary:

*Surface texture.*—The ovaries normally have a fine pubescence.

Calyx:

*Color.*—The color of the calyx is normally orange prior to petal fall.

FRUIT

Maturity when described: Firm ripe for commercial harvesting and shipment approximately June 10 to June 17 in Visalia, Calif.

Size:

*Generally.*—Large and uniform as compared to the fruit produced by other nectarine tree varieties which mature at approximately the same time of the season.

*Uniformity.*—Moderately uniform.

*Average cheek diameter.*—Approximately 65 to 78 millimeters.

*Average suture diameter.*—Approximately 60 to 69 millimeters.

*Average axial diameter.*—Approximately 65 to 69 millimeters.

Form: Variable, oval to ovate in its lateral aspect. The fruit is generally and occasionally irregularly globose in its apical aspect.

Suture:

*Generally.*—The suture appears as a distinct line which varies from about 2 to 5 millimeters in width and which extends from the base to apex. The suture normally takes on the color of the surrounding skin. The suture line is otherwise smooth and no webbing or stitching is evident. Although the suture appears along the ventral surface, it becomes more narrow and slightly folded within the stem cavity basin. Additionally, a distinct, depressed line also extends along the dorsal edge from the base to the apex.

Symmetry: Asymeterical in overall shape.

*Ventral surface.*—Generally — Irregularly shaped and distinctly lipped.

Stem cavity:

*Shape.*—Uniformly flared, rounded, and considered of moderate depth.

*Size.*—Generally medium to small in size and having a width of approximately 21 to 32 millimeters; a length of about 22 to 28 millimeters; and a depth of approximately 9 to about 11 millimeters.

Base:

*Shape.*—Broad, rounded, firm and occasionally slightly truncate. The base angle is also variable from about a right angle to being slightly oblique.

*Apex.*—Size — The apex appears raised, pointed and firm.

*Pistil point.*—Present, and further is distinctly oblique.

*Skin texture.*—Glabrous.

*Skin color.*—Generally — The skin has, as general matter, a very bright, glossy, and attractive finish.

Blush intensity and coverage: This is variable. Approximately 70% to 90% of the fruit surface is covered with same.

Blush form: Predominantly solid or washed.

Blush color: Variable, from a dark burgundy red [6-L-6], to a lighter cherry red [4-K-11] with shadings therebetween. A small amount of speckling may be present, and when it is present, it is located predominantly over the apical shoulder area.

Ground color: Variable, from creme - white [17-I-1] to creme - green [17-J-2]. The amount of ground color is approximately 10% to 30% of the fruit surface and is normally present on the basal end of the fruit.

Skin flavor: Slightly acidic.

Tenacious to flesh: Yes, at commercial maturity. There is no observed tendency for the skin to crack.

Flesh firmness: Generally — Very frim at commercially maturity.

Skin thickness: Above average.

Flesh color: White [A-1, plate 1], although some pink coloration is evident near the skin [1-K-9].

Pit cavity:

*Color.*—A slightly darker creme color [17-D-1].

Flesh texture:

*Generally.*—Considered firm and crisp at commercial maturity. A few, relatively long, lightly colored fibers are present in the flesh.

Fruit ripening: The fruit ripens at the tip first, and then along the ventral suture.

Juice production: Moderate.

Flesh flavor: Low acid and considered very sweet and well balanced.

Aroma: Present, distinct, and aromatic.

Eating quality: Very good.

Texture: Uniform, firm and creamy.

Amygdalin: Not detected.

Fruit stem:

*Size.*—Average and having a length of about 8 to 9 millimeters and a thickness of approximately 3 to 4 millimeters.

*Color.*—Oliver - Green [14-L-1] with occasional brown streaking.

STONE

Generally: Semi-freestone at commercial maturity, and fully freestone with advancing maturity.

Size:

*Generally.*—Medium as compared to other nectarine varieties.

*Average length.*—Approximately 39 to 44 millimeters.

*Average width.*—Approximately 25 to 27 millimeters.

*Average thickness.*—Approximately 21 to 25 millimeters.

Form:

*Generally.*—Variable, from slight obovate, to oval.

Stone base:

*Generally.*—The base is considered rounded, and the base angle is normally slightly oblique to the fruit axis.

Hilum:

*Shape.*—Oblong, narrow, and indented. The hilum is medium in size, oval, and appears substantially eroded.

Apex:

*Shape.*—Acute and having a sharp dentate tip.

Sides:

*Shape.*—Non-uniform.

Surface texture: Irregularly furrowed and deeply pitted. The ridges are usually most distinct over the apical shoulder. Further, numerous smaller ridges are present laterally, and near the stone base.

Fibers: A few short fibers are attached to the stone and are most frequently found around the basal area.

Ridges:

*Shape.*—Moderately rounded and interrupted.

Ventral edge:

*Shape.*—Serrated and non-uniform. The ventral edge is moerately wide, and from 6 to 8 millimeters in width at mid suture. The wings along the suture are relatively low and appear eroded.

Dorsal edge:

*Shape.*—Generally pronounced, ridged, and non-uniform. A medium width groove extends along the dorsal edge from the base to the apex. The ridges subtend the groove and are often deeply cross grooved. The upper dorsal suture is moderately eroded over the apical shoulder.

Color: Light tan [10-D-2].

Tendency to split: Moderate with both internal and external splits being observed.

Fertility: Self-fruitful.

Seed coat:

*Color.*—Brown.

Use: Fresh market for both local and long distance shipping.

Keeping quality: Good.

Shipping quality: Unknown, although the firm and crisp flesh displayed at commercial maturity indicates that the variety should have noteworthy shipping characteristics.

Resistance to disease: No particular susceptibilities were noted.

Although the new variety of nectarine tree possesses the described characteristics as a result of the growing conditions prevailing at the applicant's licensee's ranch which is located near Visalia, Calif., in the central part of the San Joaquin Valley of Central California, it is understood that variations of the usual magnitude and characteristics incident to changes in growing conditions, fertilization, pruning and pest control are to be expected.

Having thus described and illustrated my new variety of nectarine tree, what I claim as new and desired to secure by Letters Patent is:

1. A new and distinct variety of nectarine tree substantially as illustrated and described and which is somewhat similar to the Arctic Glo nectarine tree [U.S. Plant Pat. No. 7,884] which matures in approximately the same season, but which is distinguished therefrom and characterized principally as to novelty by producing fruit which have a larger size, a dark red skin color and which is semi-freestone by nature at commercial maturity.

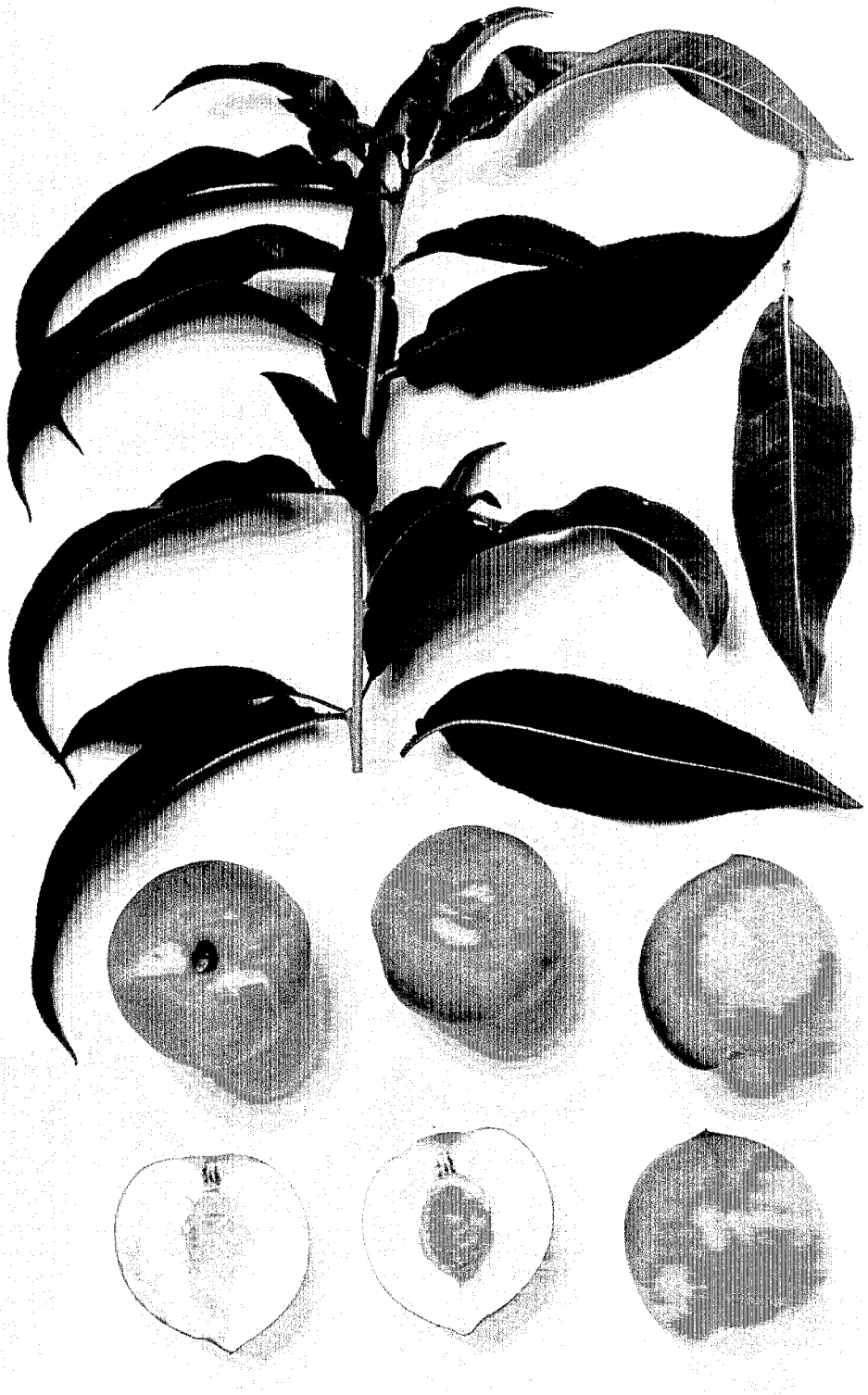

* * * * *